United States Patent [19]

Loessel et al.

[11] Patent Number: 4,825,407
[45] Date of Patent: Apr. 25, 1989

[54] METHOD AND CIRCUIT FOR CONTROLLING SINGLE CHIP MICROCOMPUTER

[75] Inventors: Mark C. Loessel; Robert W. Myers, both of Mishawaka; Robert C. Neitzke, Elkhart, all of Ind.

[73] Assignee: Miles Inc., Elkhart, Ind.

[21] Appl. No.: 166,787

[22] Filed: Mar. 2, 1988

Related U.S. Application Data

[63] Continuation of Ser. No. 916,727, Oct. 8, 1986, abandoned, which is a continuation of Ser. No. 634,573, Jul. 26, 1984, abandoned.

[51] Int. Cl.⁴ .......................... G06F 1/04; G06F 3/02; G06F 11/28
[52] U.S. Cl. ..................................... 364/900; 307/603
[58] Field of Search ....................... 364/707, 200, 900; 307/200 A, 296 R

[56] References Cited

U.S. PATENT DOCUMENTS

| | | | |
|---|---|---|---|
| 3,411,147 | 11/1968 | Packard | 364/200 |
| 3,702,463 | 11/1972 | Lesniewski | 364/200 |
| 3,941,989 | 3/1976 | McGlaughlin et al. | 364/900 X |
| 4,137,563 | 1/1979 | Tsunoda | 364/200 |
| 4,293,927 | 10/1981 | Hoshii | 364/900 |
| 4,316,247 | 2/1982 | Iwamoto | 364/200 |
| 4,322,580 | 3/1982 | Huan et al. | 364/900 X |
| 4,408,328 | 10/1983 | Wakai | 364/200 |
| 4,429,638 | 1/1984 | Kurii | 364/200 X |
| 4,463,440 | 7/1984 | Nishiura et al. | 364/900 |
| 4,479,191 | 10/1984 | Nojima et al. | 364/900 X |
| 4,481,581 | 11/1984 | Johnson | 364/200 |
| 4,545,030 | 10/1985 | Kitchin | 364/900 |
| 4,564,902 | 1/1986 | Leininger | 364/200 |
| 4,570,219 | 2/1986 | Shibukawa | 364/200 |
| 4,615,005 | 9/1986 | Maejima et al. | 364/707 X |

Primary Examiner—David L. Clark
Attorney, Agent, or Firm—Roger N. Coe

[57] ABSTRACT

A clock circuit for a microcomputer having a clock input, a halt mode state output and an interrupt input, comprises: a clock pulse generator having an output, a switch for applying a pulsed output to the interrupt input of the microcomputer to indicate a start of operation; a latch receptive of the output of the switch to change from a first state to a second state, gates receptive of the output of the clock pulse generator and the latch for applying clock pulses to the microcomputer when the logic is in the second state and preventing the application of clock pulses to the microcomputer when the logic is in the first state and circuitry for applying the halt mode state output to the logic circuit to disable same from the second state to the first state.

4 Claims, 1 Drawing Sheet

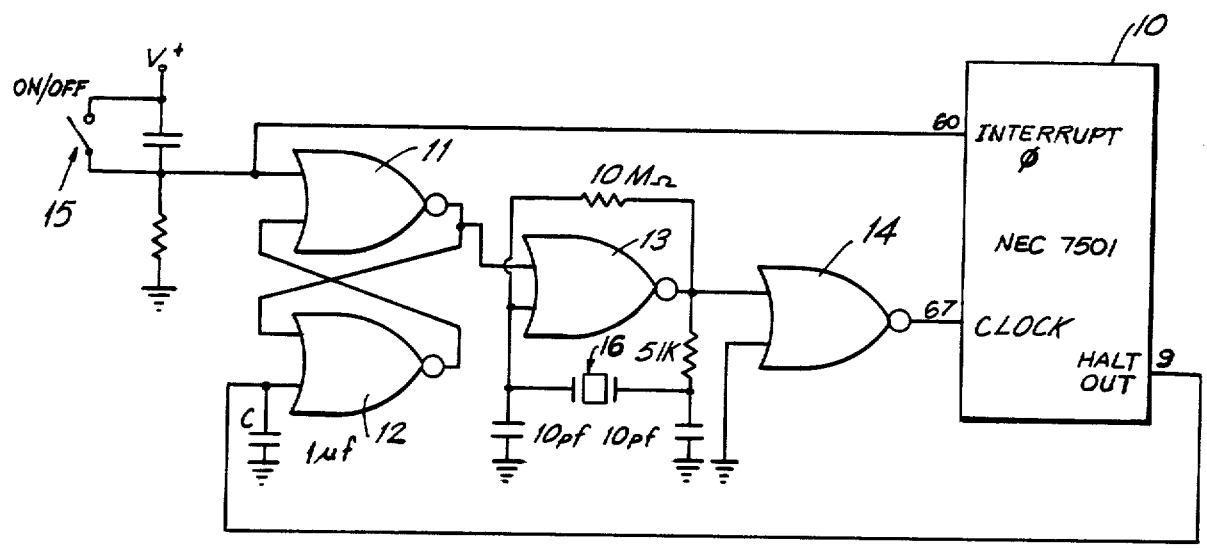

METHOD AND CIRCUIT FOR CONTROLLING SINGLE CHIP MICROCOMPUTER

This is a continuation of application Ser. No. 916,727, filed Oct. 8, 1986, which is a continuation of Ser. No. 634,573, filed July 26, 1984, both now abandoned.

BACKGROUND OF THE INVENTION

The present invention relates to a clock circuit with a power down state for use with a microcomputer.

Microcomputers, in particular integrated circuit type microcomputers such as the NEC 7501, have a clock input for providing the clock pulses necessary to operate in a conventional manner.

One disadvantage of continually applying clock pulses to the microcomputer circuitry, even when the microcomputer has halted and does not provide an output to the remaining circuitry, is that the power consumption is considerably higher than when the clock is off.

SUMMARY OF THE INVENTION

The main object of the present invention is to provide a clock circuit for use with a microcomputer for saving power consumption when the microcomputer is in a halt mode that retains memory and does not require clock pulses.

In accordance with the present invention, this and other objects are carried out by providing a circuitry which disables the clock pulses into the clock when a halt mode is sensed so as to reduce power consumption until such time as the computer returns to an operating mode.

The circuit in accordance with the present invention allows the user to turn on the microcomputer and the clock together, with the microcomputer latching the clock on. When a halt instruction is reached, the microcomputer disables the clock and after a time delay the clock turns off.

The advantage of this circuit in accordance with the present invention is that the invention allows the computer clock to be turned off to save power and the computer clock may be restarted with a minimum parts cost. In a preferred embodiment, the computer may sense the crystal frequency ramp up or a passive time constant can obliterate this window.

These and other objects and advantages of the present invention will become more apparent from the following discussion of the present invention taken with the drawing wherein:

BRIEF DESCRIPTION OF THE DRAWINGS

The FIGURE is a schematic of the clock circuit in accordance with the present invention.

DETAILED DESCRIPTION OF THE INVENTION

Referring now to the FIGURE, the microcomputer 10 is preferably a NEC 7501 having a clock input pin 67, a halt indicating output pin 9 and an interrupt 0 input pin 60. As is conventional, an on/off pushbutton 15 is provided which connects to the positive logic voltage V+ when pressed, to indicate at interrupt 0 that the microcomputer 10 is to start. The output from the pushbutton 15 is also applied to the logic formed by NOR gates 11 and 12. NOR gates 11 and 12 are initially reset to a state wherein the output of gate 11 is a logic 1 and the output of gate 12 is a logic 0. As a result the output of NOR gate 13 is a 0 and the output of NOR gate 14 is a 1.

The output of crystal oscillator 16 is fed to the input of NOR gate 13, however because of the fact that gate 11 is presenting a 1 to the input of gate 13, the output thereof is always 0. Thus no clock pulses are input to the microcomputer 10.

Upon the closing of pushbutton switch 15, an interrupt is placed at pin 60 of the microcomputer 10 and the logic formed by gates 11 and 12 is reset so that the output of gate 11 is now at a logic 0. This enables oscillator 16 to start oscillating. These pulses are thereafter inverted by gate 14 and presented to the clock input of the microcomputer 10.

The microcomputer 10 can now operate in its standard operating mode with its clock. When the microcomputer goes into a halt mode and a halt instruction is output at the corresponding output pin 9 thereof, which goes from a logic 0 to a logic 1, this will act to reset the flip-flop formed by gates 11 and 12 to disable the clock ouput of gate 13. However, due to the presence of the capacitor C at the input of gate 12, the threshold voltage for resetting the flip-flop formed by gates 11 and 12 will not be reached until after a delay which is chosen to be suitable to the microcomputer to be carry out all of the functions that must be carried out before the clock can be shut off.

The microcomputer is now in a mode where memory is retained, but power consumption is saved. If one wants to resume operation of the microcomputer 10, this can be done manually by closing on/off pushbutton 15.

It will be appreciated that the instant specification and claims are set forth by way of illustration and not limitation, and that various modifications and changes may be made without departing from the spirit and scope of the present invention.

What is claimed is:

1. A clock circuit for a single chip microcomputer having a single clock input, a halt mode state output and an interrupt input and wherein the microcomputer has a predetermined period for writing data into a memory, the circuit comprising:
    clock pulse generating means having an output;
    manually actuatable switching means for applying a pulsed output to the interrupt input of the microcomputer to indicate a start of operation;
    latching means initially in a first state and receptive of the output of the switching means to change the latching means from the first state to a second state;
    gating means receptive of the output of the clock pulse generating means and the latching means for applying clock pulses to the microcomputer when the latching means is in the second state and preventing the application of clock pulses to the microcomputer when the latching means is in the first state; and
    means for applying the halt mode state output to the latching means, after a predetermined time interval after being produced by the microcomputer to reset the latching means from the second state to the first state and thereby prevent the application of clock pulses to the microcomputer by the gating means until the latching means is changed to the second state by the manually actuated switching means at a start of operation, wherein the predetermined time interval is greater than the predetermined period for writing data into memory, said microcomputer writing into memory prior to termination of clock pulses.

2. The circuit according to claim 1, wherein the gating means includes means for gradually increasing the frequency of the clock pulses to the microcomputer from zero to the frequency of the clock pulse generating means.

3. The circuit according to claim 2, wherein the latching means comprises a set-reset flip/flop, the clock pulse generating means comprising a crystal oscillator and the switching means comprises a push-button switch.

4. A method of controlling the clocking of a single chip microcomputer having a predetermined period for writing data into a memory and having a single clock input, a first input for initiating operation of the microcomputer and a halt mode state output, by a clock circuit having an input and an output for producing clock pulses, comprising the steps of:

manually turning on the microcomputer, by applying a signal to the first input;

gating the clock circuit on; and disabling only the clock pulses to the clock input of the microcomputer after a halt mode state output is produced after a predetermined time interval from the production of the halt mode state output which time period is greater than the predetermined period for writing data into memory and preventing the application of the clock pulses to the microcomputer until repeating the step of manually turning on the microcomputer; writing into memory prior to the termination of clock pulses.

* * * * *